United States Patent [19]

Weiss et al.

[11] 4,393,002
[45] Jul. 12, 1983

[54] ε-CAPROLACTAM BLOCKED DIISOCYANATES

[75] Inventors: Jonas Weiss, Port Chester; Raymond Seltzer, New City, both of N.Y.

[73] Assignee: Ciba-Geigy Corporation, Ardsley, N.Y.

[21] Appl. No.: 360,031

[22] Filed: Mar. 19, 1982

[51] Int. Cl.$^3$ ............................................ C07D 210/00
[52] U.S. Cl. ............................................ 260/239.3 R
[58] Field of Search ................................ 260/239.3 R

[56] References Cited

U.S. PATENT DOCUMENTS

| | | | |
|---|---|---|---|
| 2,855,420 | 10/1958 | Petropoulos | 528/74 |
| 3,707,495 | 12/1972 | Mackay et al. | 260/453 P |
| 3,893,978 | 7/1975 | de Cleur et al. | 528/45 |
| 3,931,117 | 1/1976 | Leonard | 528/45 |

*Primary Examiner*—Paul Lieberman
*Assistant Examiner*—Robert E. L. Sellers
*Attorney, Agent, or Firm*—Harry Falber

[57] ABSTRACT

Powder coatings for the preparation of protective films for a wide variety of substrates, said coatings being based on urethane or epoxy systems containing a ε-caprolactam-blocked mixed 5(6)-isocyanato-1-(4′-isocyanatophenyl)-1,3,3-trimethylindane; as well as the mixed diisocyanate and the ε-caprolactam-blocked form thereof.

3 Claims, No Drawings

ε-CAPROLACTAM BLOCKED DIISOCYANATES

This invention relates to electrostatically sprayable powder coatings for use in the preparation of protective films with outstanding properties, said coatings being based on urethane or epoxy systems containing ε-caprolactam-blocked mixed diisocyanates.

Powder coatings have been known for a number of years. The initial systems comprised one-component polyurethane coatings wherein curing was accomplished by reaction of the free isocyanate group with water. Subsequently, these coating systems were based on "blocked" isocyanates. Thus, rather than relying on curing at room temperature, elevated temperatures were utilized thereby eliminating the blocking group and freeing the isocyanate groups for cross-linking in the conventional manner. Mono-functional hydroxy-containing compounds such as phenols were widely utilized in these early systems. Such a blocking approach provided greater flexibility and improved performance in terms of application and adhesion of the coating.

Caprolactam-blocked polyisocyanates were thereafter adopted as improvements over the phenol-blocked systems. Such caprolactam-blocked polyisocyanates and their use in a wide variety of powder coatings are disclosed, for example, in U.S. Pat. Nos. 3,822,239, 3,822,240, 3,849,160, 3,893,978 and 3,931,117. These patents disclose the blocking of a number of aliphatic, aromatic and cycloaliphtic polyisocyanates and the subsequent use of these blocked isocyanates with hydroxy-containing solid polymers such as polyesters, polyethers, polyurethanes, alkyd resins, vinyl polymers, epoxide resins, and the like. Advantages are attributed to these systems including improved flow and leveling of the protective film before final curing, improved surface characteristics, ready formulation with the polymer, and the like. Despite these stated advantages, it is still desirable to identify a particular blocked-isocyanate which provides excellent processing and application characteristics and which yields protective films exhibiting excellent adhesion, strength and resistance characteristics.

Accordingly, it is the primary object of this invention to identify a blocked-isocyanate material which provides the aforementioned characteristics.

It is a further object to incorporate the isocyanate into various hydroxy-containing solid polymers in order to provide improved powder coating systems.

It is another object to provide such systems for ready application by electrostatic spraying techniques.

Various other objects and advantages of this invention will be readily apparent from the following detailed description thereof.

It has now been determined that the use of ε-caprolactam-blocked mixed 5(6)-isocyanato-1-(4'-isocyanatophenyl)-1,3,3,trimethylindane in urethane and epoxy powder coating systems provides a series of unexpected performance improvements. Thus, this isomeric mixture is especially suitable for use in electrostatically sprayable powder coatings. More specifically, the 100°–108° C. melting point of this blocked diisocyanate is particularly advantageous for the melt processing operation into a powder coating. It compares favorably with the lower melting point of such commercially utilized systems as caprolactam-blocked isophorone diisocyanate. It also exhibits processing advantages over systems such as caprolactam-blocked (4,4'-diisocyanatodiphenylmethane) which does not melt below its 175° C. decomposition point. In contrast, the instant system decomposes at 175° C. to release the free isocyanate, this temperature being particularly convenient for use as the curing temperature of the applied coating.

In addition, these materials can be readily formulated with hydroxy-bearing polyesters and with epoxy resins to prepare coating systems which, in turn, can be readily applied by electrostatic spraying. The resulting urethane coatings are hard and flexible and exhibit good impact strength, chemical resistance and resistance to discoloration on overbake during curing. Likewise, the resulting epoxy coatings exhibit excellent physical and chemical properties. These coatings exhibit excellent adhesion to a wide variety of substrates, particularly to metals such as steel and aluminum. These coatings also exhibit good solvent resistance, impact strength, flexibility and hardness, thereby providing both protective and decorative coatings.

The mixed diisocyanate of the instant invention corresponds to the formula

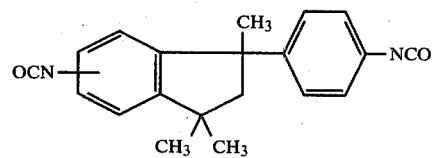

The 5- and 6-isocyanate isomers predominate in this mixture although small amounts of other isomers may also be present. In general, the mixture will contain from 10 to 80% of the 5-isomer and from 20 to 90% of the 6-isomer. Preferred values are 15 to 50% of the 5-isomer and 50–85% of the 6-isomer. The mixed diisocyanate is prepared from the corresponding diamine by reaction with phosgene. The initial isomeric mixture of diamines is fully disclosed in U.S. Pat. No. 3,983,092. In addition, the preparation of isocyanate indanes is disclosed in U.S. Pat. No. 2,855,420. It is to be noted that the pure 6-isocyanato-indane and a process for its preparation are likewise disclosed in U.S. Pat. No. 2,855,420. The procedure in U.S. Pat. No. 3,983,092 is preferred in view of its increased simplicity and economy.

The ε-caprolactam derivative of this isomeric mixture corresponds to the formula

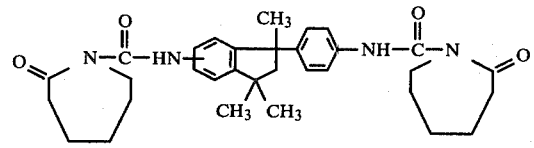

Methods for preparing such derivatives are well known to those skilled in the art and generally involve the reaction of the isocyanate with ε-caprolactam at a temperature of about 115° C. for a period of three hours. Quantitative yields of solid, blocked isocyanate are obtained, the product having a melting range of about 100°–108° C. and a decomposition point of 175° C. Preferably, about 99% of the isocyanate groups should be blocked into order to prevent premature crosslinking.

The hydroxyl group-containing polyesters, solid below 40° C. and readily flowable at 150° C. –180° C.

and forming low viscosity melts, which are used in accordance with the invention are based primarily on aromatic polycarboxylic acids. The aromatic polycarboxylic acids can be mononuclear (phenyl) or polynuclear (naphthyl, biphenyl, bis-phenyl, etc.) and contain from 6 to 20, preferably 6 to 12, carbon atoms in the ring systems. These acids can be unsubstituted or substituted with substituents such as halo, alkyl (especially alkyl of 1 to 4 carbon atoms), alkoxy (especially alkoxy of 1 to 4 carbon atoms), and the like. Part of the aromatic polycarboxylic acids may also be replaced by aliphatic and/or cycloaliphatic and/or araliphatic polycarboxylic acids.

Suitable aromatic, aliphatic, and cycloaliphatic polycarboxylic acids, wherein the aromatic polycarboxylic acids may be mononuclear or polynuclear, are, for example, oxalic acid, succinic acid, adipic acid, sebacic acid, terephthalic acid, methylterephthalic acid, 2,5- and 2,6-dimethylterephthalic acid, chloroterephthalic acid, 2,5-dichloroterephthalic acid, fluoroterephthalic acid, isophthalic acid, trimellitic acid, naphthalene dicarboxylic acid, in particular the 1,4-, 1,5-, 2,6- and 2,7-isomers, phenylene-diacetic acid, 4-carboxyphenoxy-acetic acid, m- and p-tertphenyl-4,4"-dicarboxylic acid, dodecahydrodiphenic acid, hexahydroterephthalic acid, 4,4'-diphenic acid, 2,2'- and 3,3'-dimethyl-4,4'-diphenic acid, 2,2'-dibromo-4,4'-diphenic acid, bis-(4-carboxyphenyl)-methane, 1,1- and 1,2-bis-(4-carboxyphenoxy)-ethane, bis-4-carboxyphenyl ether, bis-4-carboxyphenyl sulfide, bis-4-carboxyphenyl ketone, bis-4-carboxyphenyl sulfoxide, bis-4-carboxyphenyl sulfone, 2,8-dibenzofuran-dicarboxylic acid, 4,4'-stilbene dicarboxylic acid and octadecahydro-m-terphenyl-4,4-dicarboxylic acid, and the like. Mixtures of the aforementioned compounds may also be employed.

To make the hydroxyl group-containing polyesters, diols are preferably used as the alcohol component. Aliphatic and cycloaliphatic polyols are useful herein. Preferred are alkane and cycloalkane diols and triols containing 2 to 20 carbon atoms, preferably 2 to 12 carbon atoms. It is possible to partially also use other polyols, e.g. triols; examples for suitable compounds are: ethylene glycol, propylene glycol such as 1,2- and 1,3-propane diol, 2,3-dimethylpropane diol-(1,3), butane diols such as butane diol-(1,4), hexane diols such as hexane diol-(1,6), 2,2,4-trimethylhexane diol-(1,6), 2,4,4-trimethylhexane diol-(1,6), heptane diol-(1,7), octadene-9,10-diol-(1,12), thiodiglycol, octadecane diol-(1,18), 2,4-dimethyl-2-propyl-heptane diol-(1,3), butene diol-(1,4), diethylglycol, triethylglycol, trans-1,4-cyclohexanedimethanol, 1,4-cyclohexane diols, glycerine, hexane triol-(1,2,6), 1,1,1-trimethylol propane, and the like. Mixtures of the aforementioned compounds may also be used.

When making the polyester, the polyol is utilized in such quantities that more than one OH-group equivalent corresponds to one carboxyl group equivalent. The hydroxyl-containing polyesters can be prepared in known and conventional manner. Needless to say, numerous polyester systems are commercially available.

The blocked isocyanate can be processed with a wide variety of solid epoxy resins. Included among such resins are epoxide resins based on polyhydric phenols such as bisphenol A, F and S, and epoxidation products of phenol novolacs and cresol novolacs. These resins may contain various optional ingredients including accelerators, fillers, pigments, and the like.

The blocked isocyanates are utilized preferably in stoichiometric quantities of one mole of hydroxyl or epoxy group per mole of isocyanate group. An excess or reduced amount of reactants reflecting ±20% from the stoichiometric amounts may be used in order to vary the mechanical properties of the coatings.

As previously noted, the blocked isocyanates can also be processed with a wide variety of polyvinyl resins containing hydroxyl groups. These resins are made in known manner by copolymerization of hydroxy lower alkyl acrylates or methacrylates, such as hydroxy-propyl-(meth)-acrylic acid ester and hydroxy-ethyl(meth)-acrylic acid ester, with comonomers such as ethyl acrylate, butyl acrylate, 2-ethylhexyl acrylate, methyl methacrylate ethyl methacrylate, butyl methacrylate, lauryl methacrylate, styrene, α-methylstyrene, vinyltoluene, acrylonitrile, acrylamide, vinyl acetate, acrylic acid and methacrylic acid, in the presence of initiators and regulators.

The powder coatings are prepared by combining the components, preferably in powder form, and then melt blending in an appropriate apparatus such as a two-roll mill, an extruder, and the like. Blending temperatures ranging from 69° to 76° C. may be utilized, it being required that the temperatures be below the splitting temperature of the blocked isocyanate. The hardened solid material is then ground in a conventional mill, with all material smaller than about 75 microns generally being recovered for use.

Various optional ingredients may be included in the powder coatings. In order to avoid agglomeration over a lengthy storage period, the pulverulent coating masses can be treated with suitable agents. Applicable powderization agents for the coating masses according to the invention have to be chemically inactive with respect to the components of the coating masses. Suitable powderizing agents are, for instance, talcum or finely divided silica, which may also contain organic residues. Also suitable are finely dispersed calcium phosphate and aluminum sulfate. Applicable flowing and gloss ameliorants include polyvinyl butyrals, mixed polymers of n-butyl acrylate and vinyl isobutyl ether, ketone-aldehyde condensation resins, solid silicone resins or mixtures of zinc soaps of fatty acids and aromatic carboxylic acids. As heat stabilizers and antioxidants, commercially available, sterically hindered polyvalent phenols of high molecular weight have proven successful. Other agents may, however, also be used. Pigments may be added. The quantity of the additives employed depends on each individual case and on the desired properties.

In the method of electrostatic powder spraying, a pulverulent film forming coating material is sprayed on an article through an electrostatic field whereby the coating material adheres to the article by means of the electrostatic charge. The field used to provide the electrostatic charge must be sufficient to cause the coating material to stick to the article until it is baked to fuse the coating into a continuous surface. It is possible to modify this method by heating the article to be coated to a temperature which is above the fusion temperature of the coating material, then spraying the article with the electrostatically charged powder and baking the coated article.

As previously noted, the powder coatings can be applied to a variety of substrates, including metals such as steel and aluminum. Subsequent to application, the coated objects are subjected to temperatures from 180° to 210° C. for periods of time ranging from 5 to 30 minutes. The curing conditions can be defined according to the specific system being utilized. The free isocyanate groups thus generated react with the hydroxy groups of the polyesters or of the epoxy resins, resulting in the formation of protective films having urethane linkages.

As previously noted, these films provide excellent hardness, flexibility, strength and chemical resistance characteristics. In particular, the instant systems are unexpectedly improved over prior art -caprolactam-blocked isocyanate systems derived from isophorone diisocyanate or from 4,4'-diisocyanato-diphenylmethane, e.g. in processability, coating hardness and impact strength.

The following examples illustrate the preferred embodiments of the invention. In these examples, all parts given are by weight unless otherwise specified.

EXAMPLE I

A. Preparation of 5(6)-isocyanato-1-(4'-isocyanatophenyl)-1,3,3-trimethylindane

A compound mixture of 10 parts of 38% 5-amino-1-(4'-aminophenyl)-1,3,3-trimethylindane and 62% 6-amino-1-(4'-aminophenyl)-1,3,3-trimethylindane was dissolved in 45 parts of toluene and then slowly added to a solution of 30 parts phosgene in 65 parts of toluene, while keeping the mixture below 5° C. The mixture was heated to 55° C. over a period of 40 minutes during further phosgene addition and then allowed to react at the reflux temperature for a further period of 90 minutes. The solvent was removed yielding a pale yellow solid with melting point of 60°–80° C. Titration showed 6.04 equivalents of isocyanate per kilogram (96.1% of theory).

B. Preparation of ε-caprolactam blocked isocyanate 79.5 parts of the isocyanate prepared hereinabove were blended with 57.5 parts ε-caprolactam and allowed to react, under nitrogen, at 115° C. for a period of three hours. The solid, blocked isocyanate was recovered having a melting range of 100°–108° C. and a decomposition point of 175° C. Titration showed that all of the isocyanate groups were tied up and thus not available for reaction.

EXAMPLE II

This example illustrates the preparation of a typical powder coating formulation of this invention. The following ingredients were utilized:

|  | parts |
|---|---|
| Blocked isocyanate (Ex. I) | 53.2 |
| Polyester(1) | 100.00 |
| Titanium diioxide pigment | 76.6 |
| Flow agent(2) | 2.3 |
| Silica anti-blocking agent | 0.47 |

(1)XP-8000 from Cargill Corp.
(2)MODAFLOW II from Monsanto.

The ingredients were mixed and then melt blended on a two-role mill at 77° C. Gel times at 171° C. were then determined to ensure that no substantial curing had occurred. The resulting formulated mixture was ground in a mill and sieved to recover all materials having a particle size less than 75 microns. This product was designated Formulation 1.

EXAMPLE III

The following powder coating formulations were prepared utilizing the procedure of Example II. Compositions 4–6 reflect comparative systems.

|  | Formulation # parts | | | | |
|---|---|---|---|---|---|
|  | 2 | 3 | 4 | 5 | 6 |
| Blocked isocyanate (Ex. I) | 96.0 | 35.6 | — | — | — |
| Polyester(1) | — | — | 100.0 | — | — |
| Polyester(3) | 100.0 | — | — | 100.0 | — |
| ε-Caprolactam blocked isophorone diisocyanate(4) | — | — | — | 79.0 | — |
| ε-Caprolactam blocked isophorone diisocyanate(5) | — | — | 22.0 | — | 29.4 |
| Solid epoxy resin(6) | — | 100.0 | — | — | 100.0 |
| Titanium dioxide pigment | 92.3 | 67.8 | 61.0 | 92.5 | 64.8 |
| Flow agent(2) | 2.7 | 2.0 | 1.8 | 2.7 | 2.0 |
| Silica anti-blocking agent | 0.49 | 0.41 | 0.37 | — | 0.39 |

(3)Polyester 1137 from Veba-Chemie
(4)B-989 from Veba-Chemie
(5)CR-10 from Cargill, Inc.
(6)Araldite GT-7014 from CIBA-GEIGY Corp.

EXAMPLES IV

The performance characteristics of the formulations of Examples II and III were determined according to the following test procedures.

The powders were electrostatically sprayed on 25 mil anodized aluminum panels which were then heated in a circulating air oven, as per the indicated optimized cure schedule. The resulting cured panels were then tested.

Reverse Impact—See ASTM D-2794 (weight dropped on uncoated surface)

Mandrel Bend—See ASTM D-3111

Adhesion—Eleven parallel cuts (1–2 mm. apart and 3 cm. long) are made in the coated surface of the panel with a sharp razor blade. Eleven cuts of similar dimension are then made perpendicular to and intersecting with the first cuts. A strip of adhesive tape is pressed firmly over the score lines and then pulled off rapidly toward the tester (perpendicular to the plane of the panel). The number of squares retained on the panel is noted.

MEK Resistance—A Scott "C-fold" paper towel is saturated with 2-butanone and rubbed by hand back and forth across the coated surface of the panel. Any observable removal or significant dulling of the coating after 100 back and forth strokes is recorded as a failure.

Specular Gloss—Specular gloss is read directly on a Hunter D48D Glossmeter, at an angle of 60°.

Surface Appearance—The surface of the cured coating is visually observed and rated according to the following scheme:

1—uniform appearance (excellent flow-out)
2—slight orange peel—i.e. surface texture of an orange peel
3—moderate orange peel
4—variable gloss characteristics
5—spotted surface (non-uniform flow)

Pencil Hardness—See ASTM D3363

Blocking Resistance—The coating powder is stored in an open container in an oven at 40° C. The time to lump formation and absence of free flow is noted.

|  | Formulation # | | | | |
| --- | --- | --- | --- | --- | --- |
|  | 1 | 2 | 4 | 5 | A |
| Optimized Cure Schedule (min/°C.) | 15/210° | 15/210° | 30/182° | 15/200° | 20/180° |
| Film Thickness (mils) | 1.8 | 1.2 | 1.5 | 1.5 | 1.2 |
| Reverse Impact (in.-lbs.) | >160 | 120 | >160 | 20 | 20 |
| Mandrel Bend Pass at: | 1/8″ | 1/4″ | 1/8″ | 1/8″ | 1/4″ |
| Cross-Cut Adhesion % Retained | 100 | 100 | 100 | 100 | 100 |
| MEK Resistance - 100 double rubs | Pass | Pass | Pass | Pass | Pass |
| Specular Gloss (60°) | 73 | — | 85 | 82 | 58 |
| Film Surface Appearance | 4 | 5 | 1-2 | 1 | 5 |
| Pencil Hardness | 3H | 6H | 2H | 3H | 5H |
| Resistance to Blocking at 40° C. (Weeks) | >10 | >10 | >10 | >10 | >10 |

A — formulated 4,4′-diphenylmethane diisocyanate - based polyester powder coating.

|  | Formulation # | | |
| --- | --- | --- | --- |
|  | 3 | 3 | 6 |
| Optimized Cure Schedule (min/°C.) | 20/190° | 10/200° | 30/200° |
| Film Thickness (mils) | 1.0 | 1.0 | 1.3 |
| Reverse Impact (in.-lbs.) | >160 | >160 | <4 |
| Mandrel Bend Pass at: | 1/8″ | 1/4″ | 1/2″ |
| Cross-Cut Adhesion % Retained | 100 | 100 | 100 |
| MEK Resistance - 100 double rubs | Pass | Pass | Dulls |
| Specular Gloss (60°) | 90 | 81 | 88 |
| Film Surface Appearance | 1-2 | 1-2 | 1 |
| Pencil Hardness | 4H | 3H | 2H |
| Resistance to Blocking at 40° C. (Weeks) | >10 | >10 | 1-2 |

These results indicate that the powder coatings of the instant invention generally show to advantage in such important properties as hardness, impact strength, solvent resistance and blocking resistance. These improvements are particularly to be noted in the epoxy resin systems.

In summary, this invention provides satisfactory powder coating formulations based on blocked diisocyanates. Variations may be made in procedures, proportions and materials without departing from the scope of the invention as defined in the following claims.

What is claimed is:

1. A ε-caprolactam-blocked diisocyanate isomeric mixture corresponding to the formula

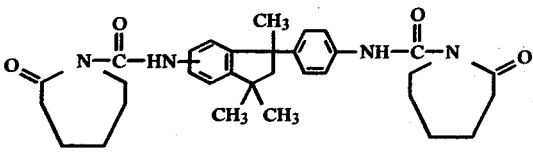

said mixture comprising from about 10 to 80% of the 5-isomer and from about 90 to 10% of the 6-isomer.

2. The mixture of claim 1, which comprises from 15 to 50% of the 5-isomer and 50–85% of the 6-isomer.

3. The mixture of claim 2, which comprises 38% of the 5-isomer and 62% of the 6-isomer.

* * * * *